United States Patent [19]

James

[11] Patent Number: 5,279,551
[45] Date of Patent: Jan. 18, 1994

[54] TROCAR CATHETER

[75] Inventor: George K. James, Tampa, Fla.

[73] Assignee: Vascular Products, Inc., Palm Harbor, Fla.

[21] Appl. No.: 827,412

[22] Filed: Jan. 29, 1992

[51] Int. Cl.$^5$ .................. A61M 5/00; A61M 25/00
[52] U.S. Cl. ................................. 604/44; 604/164; 604/180
[58] Field of Search .................. 604/43, 44, 164, 170, 604/280

[56] References Cited

U.S. PATENT DOCUMENTS

| | | | |
|---|---|---|---|
| 256,950 | 4/1882 | Pfarre | 604/43 |
| 3,190,290 | 6/1965 | Alley et al. | 604/280 |
| 4,027,659 | 6/1977 | Slingluff | 604/280 X |
| 4,469,483 | 9/1984 | Becker et al. | 604/280 |
| 4,559,046 | 12/1985 | Groshong et al. | 604/170 X |
| 4,842,583 | 6/1989 | Majlessi | 604/43 |
| 5,009,636 | 4/1991 | Wortley et al. | 604/43 |

FOREIGN PATENT DOCUMENTS

| | | | |
|---|---|---|---|
| 921576 | 4/1982 | U.S.S.R. | 604/43 |
| 2032780 | 5/1980 | United Kingdom | 604/43 |

*Primary Examiner*—Randall L. Green
*Assistant Examiner*—Mary Beth Jones
*Attorney, Agent, or Firm*—Eugene E. Renz, Jr.

[57] ABSTRACT

A catheter device useful for treatment of the pleural space. The device includes a catheter tube having an internal end and an external end and is sized for use in the pleural space. The tube has a central bore forming a first lumen with a flared suction engaging portion on the external end and a tapered portion on the internal end for providing access to the pleural space. Also included is a stylette sized for insertion in the first lumen, the stylette having less flexibility than the tube. Forming part of the device is a second lumen axially extending in the catheter tube from the external end to a closed terminal point proximate the internal end of the tube and having a substantially smaller diameter than the first lumen, the second lumen having at least one opening proximate the closed terminal point, the second lumen being fitted with a flexible tube having an injection port at its exterior end and an open end bonded to the internal wall of the second lumen. The device further includes an axially extending radiopaque stripe extending along the tube at a location 180° from the second lumen.

1 Claim, 2 Drawing Sheets

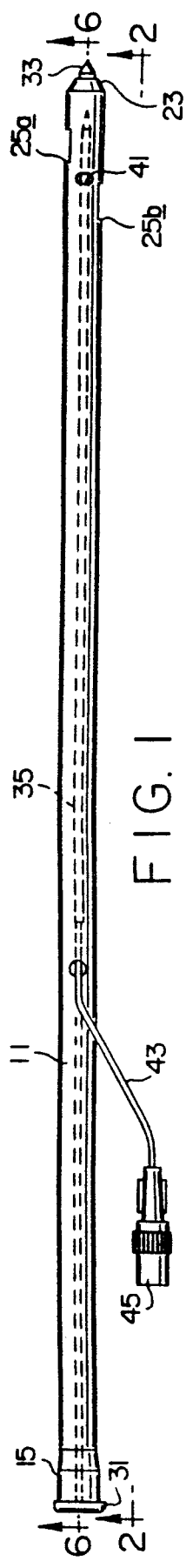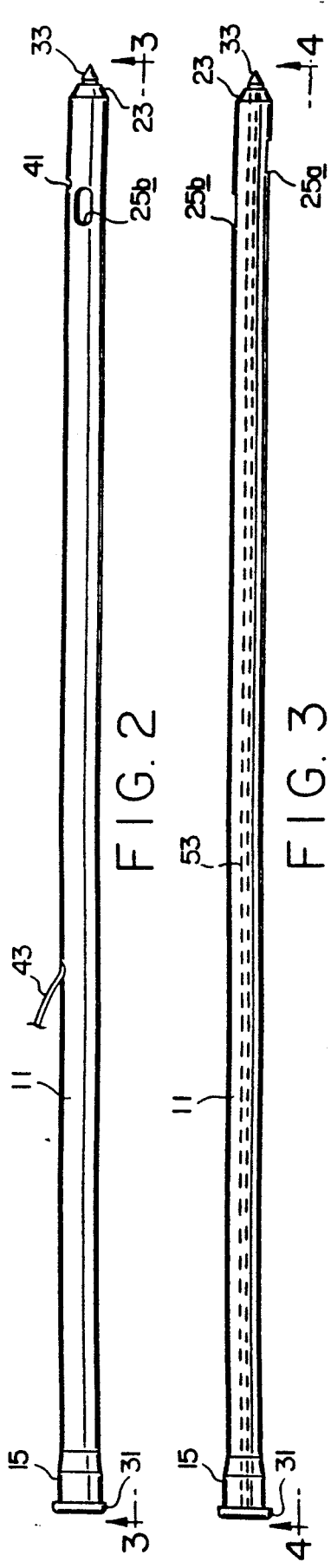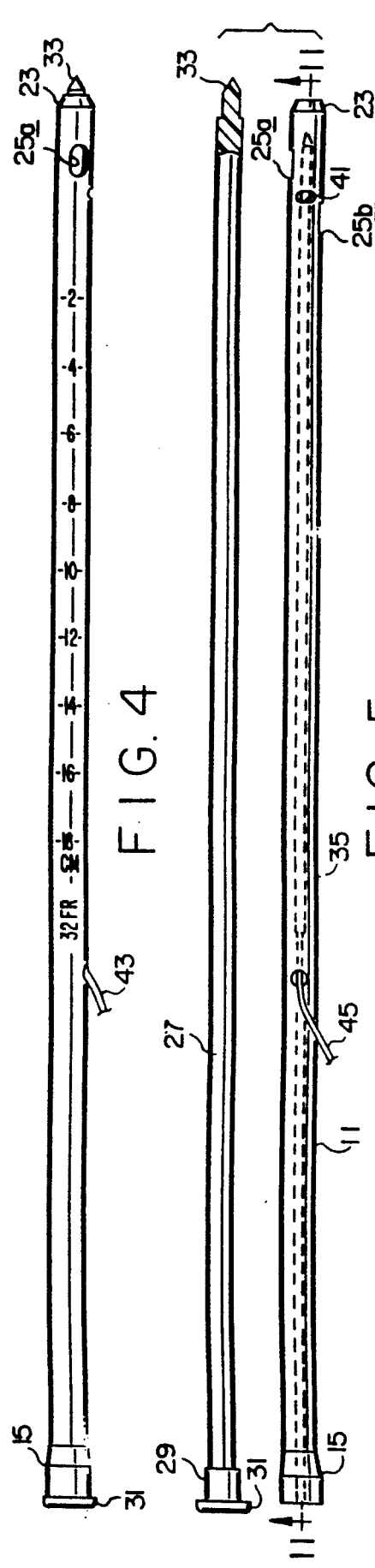

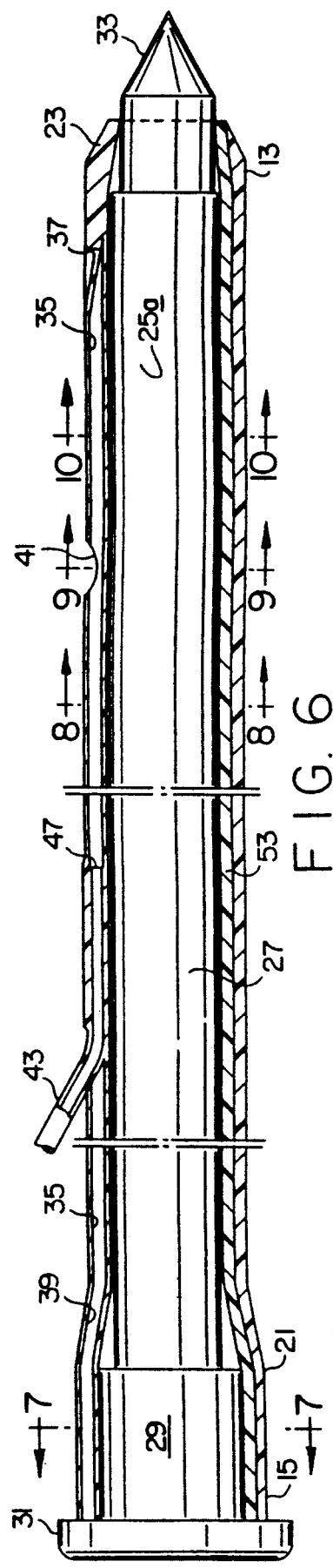
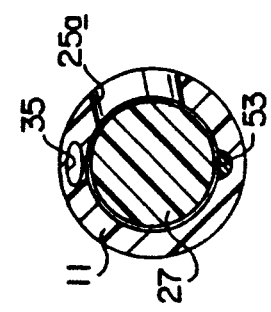
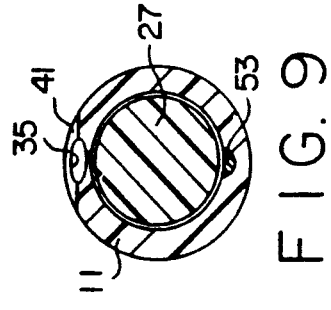
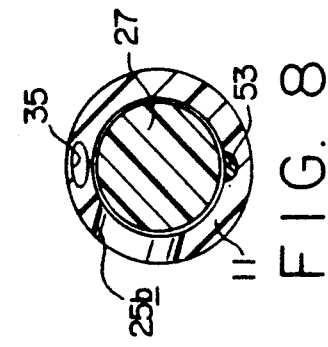
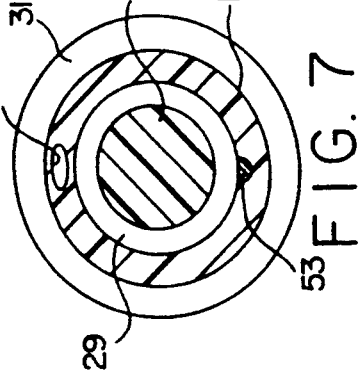
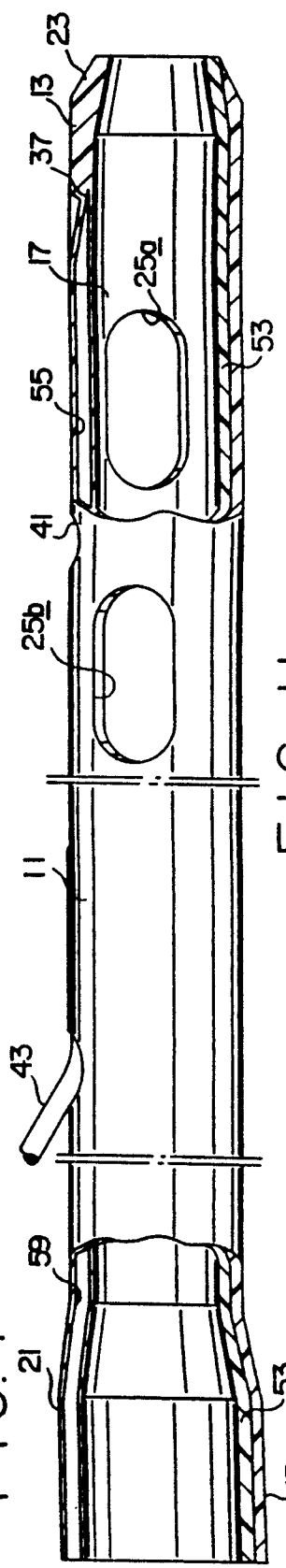

performed on the patient. Nevertheless, there is often a need to give pain relief just at the time when vacuum is most needed. Also, antibiotic treatment is often performed simultaneously with evacuation of fluids, sometimes requiring two catheters to be inserted if treatment cannot be given by syringe. Here particularly, direct application at the point of need is not possible using a syringe.

TROCAR CATHETER

FIELD OF THE INVENTION

The present invention relates to a catheter used for evacuation of fluid, blood and air from the pleural space. More particularly, the invention relates to a trocar catheter in which improved treatment is achieved by the use of an additional lumen for multiple purposes such as irrigation, introduction of drugs and treatment fluids without interruption of the primary lumen as it is used for suction and evacuation.

BACKGROUND OF THE INVENTION

Catheters have been used for many years to remove body fluids, whereby a sharp pointed instrument is fitted with a cannula and used to insert the cannula into a body cavity as a drainage outlet. Trocar catheters are used for evacuation of fluid, blood and air from the pleural space. Interpleural irrigation is one technique used following thoracotomy to reduce cough and sign reflexes.

This is a common practice of placing an intake into a body cavity of a patient and to place the tube in communication with a vacuum source to drain fluids from the cavity. The vacuum may be a manually operated syringe but more commonly is a wall outlet of a vacuum system if that is available. One such device is shown in Friend U.S. Pat. No. 3,982,546 in which a reservoir is used in communication with passages to accumulate fluids, particularly the bladder in this case. This patent is intended to prevent discharge of drainage fluid without releasing the fluid to the environment when normal discharge is interrupted. A special reservoir is used for this purpose.

Another design which employs a second lumen is shown in Sheridan U.S. Pat. No. 3,599,641. This design does not employ a stylette and is not open on the distal end. It has no injection port for secondary treatment and employs a single molded part. This patent is designed to have quick and sterile connections for multiple purposes. While these designs are useful in surgical procedures, such designs have not met with commercial success in some uses because of the difficulty of precisely inserting and locating the catheter.

Allen U.S. Pat. No. 4,810,244 discloses an improved trocar having plural cannula for washing and draining under microscopic observation. It is specifically designed for extremely small procedures, usually under microscopic observation, whereby two cannula are connected so that wash fluids may be added by one and removed by the other to provide a continuous circuit of fluid flow. The particular procedure which is of interest in Allen is extraction of oocyctes from follicles in human ovaries, and the device uses inner and outer cannula so that the inner cannula can penetrate the follicle being drained. The outer ends of the cannula are connected.

Other catheter devices which are used in the medical field are shown in: Roberts U.S. Pat. No. 3,459,188 for abdominal use; Gay et al U.S. Pat. No. 5,047,018 for heart procedures; Rudie U.S. Pat. No. 3,804,097 for abscess treatment; and Kopp U.S. Pat. No. 4,073,297 for arterial and vein insertion.

None of the prior art designs are directed at the very serious problems incurred in pleural surgery where large quantities of fluids, blood and air are to be removed from patients of various ages and sizes. The discomfort and pain caused by loss of vacuum at any time can seriously affect procedures being performed on the patient. Nevertheless, there is often a need to give pain relief just at the time when vacuum is most needed. Also, antibiotic treatment is often performed simultaneously with evacuation of fluids, sometimes requiring two catheters to be inserted if treatment cannot be given by syringe. Here particularly, direct application at the point of need is not possible using a syringe.

Accordingly, it is an object of the present invention to provide a safe and simple method to apply vacuum to pleural cavities.

Another object of this invention is to provide a device which is suitable for simultaneous evacuation and irrigation of the interior pleural region of the body without additional discomfort and without interference with either procedure.

Yet another object of the present invention is to provide a device capable of locally administering drugs and pain relief at a point of need while that region is being evacuated by vacuum.

Other objects will appear hereinafter.

SUMMARY OF THE INVENTION

It has now been discovered that the above and other objects of the present invention may be accomplished in the following manner. Specifically, the present invention provides a catheter device useful for treatment of the pleural space. The device includes a catheter tube having an internal end and an external end with the tube being formed from a clear, flexible medically inert material and sized for use in the pleural space. The tube has a central bore forming a first lumen with a flared suction engaging portion on the external end and a tapered portion on the internal end for providing access to the pleural space.

The catheter tube includes at least one opening in the first lumen at the internal end of the tube and spaced axially from the tapered portion for providing additional access to the pleural space. Preferably, the catheter tube includes a pair of openings in the first lumen at the internal end of the tube which are spaced axially from the tapered portion for providing additional access to the pleural space.

Also included is a stylette sized for insertion in the first lumen, the stylette having less flexibility than the tube. In a preferred embodiment, the stylette has a plug for engagement with the suction engaging portion of the tube to provide a surface for application of axial pressure and a sharp pointed tip for extension beyond the tapered portion in the internal end of the tube to facilitate insertion into the pleural space upon application of the axial pressure.

Forming part of the device is a second lumen axially extending in the catheter tube from the external end to a closed terminal point proximate the internal end of the tube and having a substantially smaller diameter than the first lumen. The second lumen has at least one opening proximate the closed terminal point. Preferred are two openings in the first lumen, with the pair of openings in the first lumen being spaced axially such that one of the pair is axially internal of the one opening in the second lumen and the other of the pair is axially external of the one opening in second lumen.

The second lumen is fitted with a flexible tube having an injection port at its exterior end and an open end bonded to the internal wall of the second lumen. Preferred is to have the flexible tube in the second lumen be bonded to the internal wall to form a seal preventing fluid flow past the flexible tube toward the external end of the tube.

The device further includes an axially extending radiopaque stripe extending along the tube at a location 180° from the second lumen.

BRIEF DESCRIPTION OF THE DRAWINGS

For a more complete understanding of the invention, reference is hereby made to the drawings, in which:

FIG. 1 is a plan view of an integrated suction and irrigation trocar catheter, all in accordance with the invention.

FIG. 2 is a side elevational view taken along the line 2,2 of FIG. 1.

FIG. 3 is a bottom plan view taken along the line 3,3 of FIG. 2.

FIG. 4 is a side elevational view taken along the line 4,4 of FIG. 3.

FIG. 5 is a composite plan view of both the stylette and the catheter body of the present invention.

FIG. 6 is an enlarged, sectional elevational view taken on the line 6,6 of FIG. 1 with portions of continuous detail removed in order to show small details of importance at an enlarged scale.

FIG. 7 is a transverse sectional view taken on the line 7,7 of FIG. 6.

FIG. 8 is a transverse sectional view taken on the line 8,8 of FIG. 6.

FIG. 9 is a transverse sectional view taken on the line 9,9 of FIG. 6.

FIG. 10 is a transverse sectional view taken on the line 10,10 of FIG. 6.

FIG. 11 is an enlarged, sectional elevational view taken on the line 11,11 of FIG. 5 with portions of continuous detail removed in order to show small details of importance at an enlarged scale.

DETAILED DESCRIPTION OF THE PREFERRED EMBODIMENT

As shown in the drawings, a catheter device 10 generally is of appropriate size and shape for use in the treatment of the pleural space. The device 10 is particularly suitable for use as a trocar catheter, which is used for evacuation of fluid, blood and air from the pleural space as part of treatment or after surgery. Interpleural irrigation is a technique used following thoracostomy. It reduces cough and sign reflexes. It is intended that the device of this invention be placed percutaneously or interoperatively.

The specific device shown includes a tube 11 having an internal end 13 and an external end 15, with the internal end clearly being that end which enters the patient. The tube 11 is formed from clear, flexible medically inert material and is sized for use in the pleural cavity. Accordingly, there may be a need to have several sizes as appropriate for infants, children, and adults of various sizes. The device is also intended to be used in the treatment of animals.

Catheter tube 11 includes a first lumen 17 which is formed by central bore 19 of tube 11. Lumen 17 is provided with a flared suction engaging portion 21 on the external end 15 of tube 11 and has a tapered portion 23 on the internal end 13 for providing access to the pleural space. Tapered portion 23 of tube 11 has a pair of openings 25a and 25b for providing access by the first lumen 17 to the pleural space. Openings 25a and 25b are spaced axially from tapered portion 23 to provide additional access to the region being treated.

Also forming part of the device 10 is a stylette 27 which is sized for insertion into first lumen 17. Stylette 27 normally has less flexibility than tube 11 in order to maintain rigidity as the device is inserted into the patient. As shown in FIG. 5, the stylette 27 can be removed from tube 11, such as after the unit has been placed in the person. Stylette 27 includes a plug 29 which has a flat surface 31 for application of axial pressure. Stylette 27 also has a sharp pointed tip 23 to penetrate the outer regions of the patient as the device is placed percutaneously in patients.

Also shown in FIG. 6 is a second lumen 35 which extends axially along tube 11 from the external end 15 to a closed terminal point 37 which is proximate the internal end 13 of tube 11. Lumen 35 is spaced radially outward from lumen 17 and they are not connected. Closed terminal point 37 is sealed and prevents fluids in second lumen 35 from passing further in the internal direction. It is noted that second lumen 35 has a much smaller diameter 39. Diameter 39 is, however, fully large enough to permit use of second lumen 35 to irrigate the chest cavity or to otherwise introduce medication through at least one opening 41 in lumen 35. Second lumen opening 41 is spaced axially such that one opening 25a of the pair of openings 25 in first lumen 17 is axially internal of the opening 41 and the other opening 25b is axially external of that opening 41.

Second lumen 35 is also fitted with a flexible tube 43 having an injection port 45 on the outside or external end of tube 43. This injection port 45 is of conventional design, such as those known as heparin lock ports, and is used for injection of drugs, antibiotics, antiseptic and anesthetic fluids, irrigation fluids and the like as needed in the pleural cavity. Flexible tube 43 also has an open end 47 which is bonded to the internal wall 49 of second lumen 35 to form a seal to prevent fluid flow past the tube 43 toward the external end 15 of tube 11. This is illustrated in detail in FIG. 6.

It is often desirable to place trocar catheters in the patient with a high degree of accuracy. As shown in FIG. 6, an axially extended radiopaque stripe 53 extends along tube 11 from the internal end 13 to the external end 15, and is located 180° from the second lumen 35.

As shown in FIG. 6, stripe 53 is actually a solid ribbon of radiopaque material. FIGS. 7-10 show the 180° relationship of axially extending lumen 35 and stripe 53. FIGS. 8 and 10 show the relationship of openings 25a and 25b of first lumen 17, while FIG. 9 shows the positioning of opening 41 in second lumen 35.

Shown in FIG. 11 is the relationship of the plurality of openings into the pleural section of the patient. When suction is applied to the external end 15 of tube 11, fluids, blood, and air are evacuated from the patient via the hole in the tapered portion 23 of internal end 13 of tube 11, as well as via openings 25a and 25b in the central bore 19 of first lumen 17. Treatment can continue simultaneously with irrigation, medication or anesthesia since second lumen 35 can be injected with any desired fluid or other material via injection port 45. Medical personnel no longer need to disconnect the tube from the suction device to irrigate or introduce medications. This is expected to reduce the possibility of infections or discomfort to the patients. This will be equally true when drugs are added to combat infection or pain. Because of the stripe 53, precise location of opening 41 in second lumen 35 is possible for direct topical treatment.

The present invention is useful for administration of analgesic agents to control post-operative pain following thoracotomy. It is expected to benefit patients during interpleural instillation of sclerosing agents for control of recurrent pleural effusion. It is intended for use in pleural instillation of lytic agents for loculated acute empyema and for intrapleural delivery of chemotherapeutic agents.

The present invention is useful as a conventional chest tube at the time of thoracotomy. It is also useful as a thoracostomy tube for pleural effusion or pneumothorax, following usual aseptic technique used for insertion of the chest tube.

While particular embodiments of the present invention have been illustrated and described, it is not intended to limit the invention, except as defined by the following claims.

I claim:

1. A trocar catheter device useful for treatment of the pleural space, comprising:

a catheter tube having an internal end and an external end, said tube being formed from a clear, flexible medically inert material and sized for use in the pleural space, said tube having a central bore forming a first lumen with a flared suction engaging portion on the external end and a tapered portion having an opening on the internal end for providing percutaneous access to said pleural space, said catheter tube including a pair of openings in said first lumen at the internal end of said tube and spaced axially from said tapered portion for providing additional access to said pleural space;

a stylette sized for insertion in said first lumen and having substantially the same cross-section as said first lumen, said stylette having less flexibility than said tube, said stylette having a plug for engagement with said suction engaging portion of said tube to provide a surface for application of axial pressure and a sharp pointed tip for extension beyond said tapered portion opening in said internal end of said tube to facilitate percutaneous insertion into the pleural space upon application of said axial pressure;

a second lumen axially extending in said catheter tube from said external end to a closed terminal point proximate said internal end of said tube and having a substantially smaller diameter than said first lumen, said second lumen having only one opening proximate said closed terminal point, said pair of openings in said first lumen being spaced axially such that one of said pair is axially internal of said one opening in said second lumen and the other of said pair is axially external of said one opening in said second lumen, said second lumen being fitted with a flexible tube having an injection port at its exterior end and an open end bonded to the internal wall of said second lumen, said flexible tube in said second lumen being bonded to said internal wall to form a seal preventing fluid flow past said flexible tube toward said external end of said tube; and an axially extending radiopaque stripe extending along said tube at a location 180° from said second lumen to permit precise location of said one opening in said second lumen with respect to a particular location in said pleural space to permit topical treatment at said particular location, said pair of openings in said first lumen being spaced circumferentially from said one opening in said second lumen such that one of said pair is circumferentially spaced in one direction generally between said one opening in said second lumen and said radiopaque stripe and the other of said pair is circumferentially spaced in the other direction between said one opening in said second lumen and said radiopaque stripe to thereby position said pair of openings in said first lumen in substantially diametrically opposed locations.

* * * * *